(12) United States Patent
Rieu et al.

(10) Patent No.: US 6,264,686 B1
(45) Date of Patent: Jul. 24, 2001

(54) INTRAVASCULAR STENT INTENDED IN PARTICULAR FOR ANGIOPLASTY

(76) Inventors: Régis Rieu, 33, Boulevard Gavoty, Marseille 13012 (FR); Patrice Bergeron, 38, boulevard Lei-Roure, Marseille 13009 (FR)

( * ) Notice: Subject to any disclaimer, the term of this patent is extended or adjusted under 35 U.S.C. 154(b) by 0 days.

(21) Appl. No.: 09/028,903

(22) Filed: Feb. 24, 1998

(30) Foreign Application Priority Data

Aug. 24, 1995 (FR) .................................................. 95 10061
Jul. 26, 1996 (FR) ..................................... PCT/FR96/01185

(51) Int. Cl.[7] .................................................. A61F 2/06
(52) U.S. Cl. ......................................... 623/1.16; 623/1.15
(58) Field of Search ................................. 623/1, 12, 1.15, 623/1.16; 606/108, 192, 194, 195

(56) References Cited

U.S. PATENT DOCUMENTS

| | | | | |
|---|---|---|---|---|
| 3,155,095 | * | 11/1964 | Brown | 623/1 |
| 5,496,365 | * | 3/1996 | Sgro | 623/1 |
| 5,643,339 | * | 7/1997 | Kavteladze et al. | 623/1 |
| 5,667,486 | * | 9/1997 | Mikulich et al. | 623/1 |
| 5,725,572 | * | 3/1998 | Lam et al. | 623/1 |
| 5,800,519 | * | 10/1998 | Sandock | 623/1 |
| 5,800,520 | * | 9/1998 | Fogarty et al. | 623/1 |
| 5,893,887 | * | 4/1999 | Jayaraman | 623/1 |

FOREIGN PATENT DOCUMENTS

| | | |
|---|---|---|
| 41 09 014 | 9/1992 | (DE) . |
| 0 566 807 | 10/1993 | (EP) . |
| 0 622 059 | 11/1994 | (EP) . |
| 2 678 508 | 1/1993 | (FR) . |

* cited by examiner

Primary Examiner—Bruce Snow

(57) ABSTRACT

An expandable, open-work intravascular stent, having a variable-length of generatrices and an arrangement of radio-paque marker points, is particularly suited for angioplasty as the stent reinforces vessels at bifurcation points while maintaining satisfactory hydrodynamics.

3 Claims, 1 Drawing Sheet

INTRAVASCULAR STENT INTENDED IN PARTICULAR FOR ANGIOPLASTY

BACKGROUND OF THE INVENTION

1. Field of the Invention

The present invention relates to an intravascular stent particularly intended for angioplasty.

This type of prosthesis is known as, for example, a PALMAZ stent (registered trademark) marketed by JOHNSON & JOHNSON and is described in the article "Introduction to intravascular stents" by Richard A. SCHATZ published in "CARDIOLOGY CLINICS" Vol. 6 No. 3 August 1988". These stents are made up of a material which allows for radial expansion with a balloon probe. They have an open-work casing, for example in diamond shape, which enables such expansion to take place and to increase the free arterial surface of the metal after implanting. They are intended to support the vascular wall.

In most cases this type of stent is satisfactory. However, when it is implanted near a bifurcation, its end may sometimes project into the medullary canal of the unaffected branch causing a disturbance to blood flow.

It has nevertheless come to light that stents placed near a branch point undergo irregular, often incomplete endothelialisation, unlike implants placed on straight vessels such as femoral vessels.

Surgeons consider that stents must not prolapse and therefore implant them slightly behind the bifurcation which means that the affected area is not fully covered even though it often extends into part of the other branch.

2. Description of Related Art

To overcome this drawback, in an article entitled "Aortic bifurcation stenosis: treatment with intravascular stents" published in "RADIOLOGY-JVIR, Vol. 2, No. 3, August 1991, pp 319–323, it was proposed to implant a stent in both stenosed branches and to bring the ends of both stents parallel to each other into the common branch of the vessels. With this solution it is possible, it is true, to cover all affected areas and to maintain substantially laminar blood flow, but it has the disadvantage of substantially reducing the effective section of the common branch and can only be used for vessels that are sufficiently wide.

French patent FR2678508 also proposed a stent comprising an elongated reinforcement which fits inside the inner wall of the vessel to be reinforced. In order to achieve continuous junctions, especially at bifurcations, at least two devices are provided comprising self-locking spirals with which continuous connections can be made.

Another French patent published under number FR2671280 describes a stent made up of several modular units each comprising flexible, elastic longitudinal axes connected together by enmeshed "V" fibres giving a fishbone appearance; 2, 3 or more units connected together longitudinally form an elastic cylinder. This device may be passed into an artery with a catheter and an application device which is used to stretch the open-work cylinder to reduce its diameter and then to allow it to resume its initial shape.

These types of stent do not solve the problem of the invention and are also difficult and costly to manufacture.

SUMMARY OF THE INVENTION

The object of the invention is to overcome these various disadvantages by proposing an improved stent which can be used to reinforce vessels at bifurcation points while maintaining satisfactory hydrodynamics.

For this purpose the invention particularly relates to a vascular stent having the general shape of an expanding open-work cylinder characterized in that the length of the generatrices of the expanded stent, measured in relation to a specified transverse plane, is not constant.

According to one variant, at least one of the ends of the open-work cylinder is substantially bevelled.

At least one of the frontal ends terminates in a plane forming with the longitudinal axis an angle of less than 90°, preferably an angle of between 30° and 60°.

According to a second variant of embodiment, at least one of the frontal ends has the shape of an intersection between two perpendicular cylinders.

According to a third variant of embodiment, at least one of the frontal ends, from the front view, has a "V" section. With this form of embodiment it is possible to insert an implant in a common branch and to connect it to two stents of the first or second variants implanted in the secondary branches.

Advantageously, the stent of the invention comprises radiopaque marker points forming a trihedron for position identification at the time of implanting.

BRIEF DESCRIPTION OF THE DRAWINGS

The invention will be more clearly understood on reading the description of a non-restrictive example of embodiment given below with reference to the appended drawings in which.

DETAILED DESCRIPTION OF THE INVENTION

Figure 1:
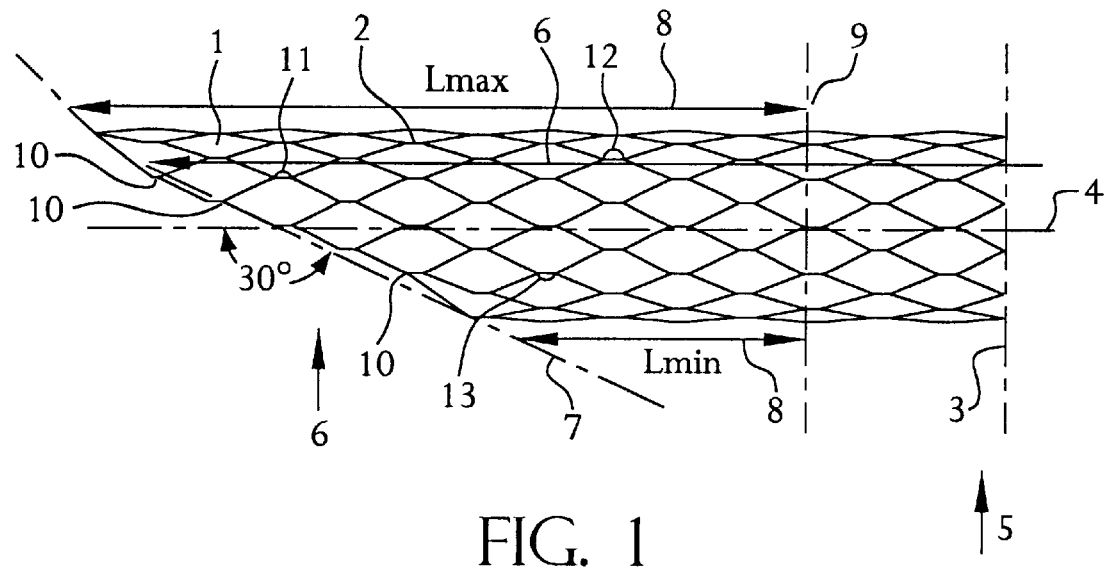
FIG. 1 represents a front view of a stent according to the invention.

The stent is made up of an open-work cylinder in stainless steel with a non-expanded diameter of 3.1 millimetres and an expanded diameter of 8 millimetres. It has a network of polygonal openings (1) and knots (2). The back end (5) terminates in a transverse plane (3) perpendicular to the longitudinal axis (4).

The front end (6) terminates in a bevelled shape. It is bordered by a plane (7) forming with the longitudinal axis (4) an angle of approximately 30°. The length of generatrices (8), measured from a specified transverse plane (9), for example the median plane, of the casing of the open-work tubular body varies between a minimum value Lmin and a maximum value Lmax.

The bevelled end (6) is cut level with knots (10).

Three radiopaque marker points (11 to 13) outline a trihedron to identify orientation when implanting and to allow repositioning before expansion.

Figure 2:
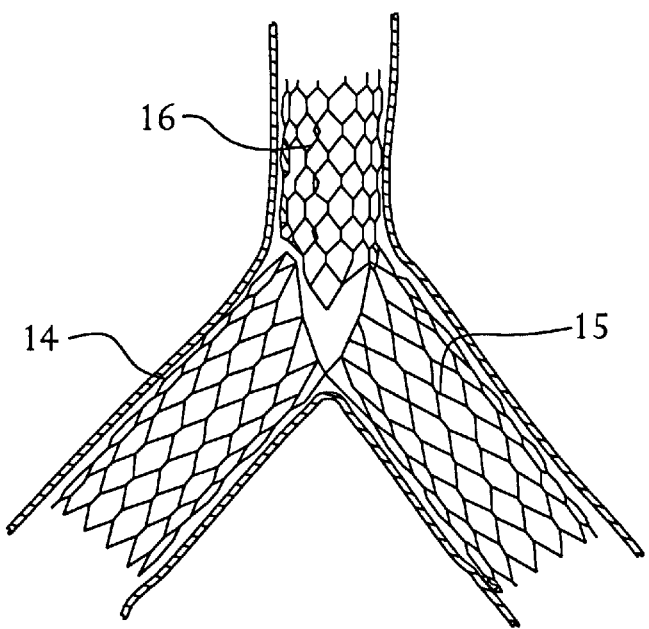
FIG. 2 represents a section diagram of an example of implantation at a vascular bifurcation.

FIG. 2 represents a section diagram of an example of implantation at a vascular bifurcation. In this example, two stents are used (14,15) one of a first type which, from the front view, has one end cut along a plane forming an angle of approximately 50 degrees in relation to the longitudinal axis, and a stent of the second type (16) having one end cut along two planes and which, from the front view, has a "V" shape.

The invention as described above is given for illustration purposes and is non-restrictive. Needless to say the artisan will be able to achieve different variants while remaining within the limits of the invention.

What is claimed is:

1. A system for maintaining a patient lumen at a bifurcation of an anatomic canal comprising:

two slanted-end stents each of which comprises a radially expanded mesh structure substantially forming a cylinder having a longitudinal axis, a back end defined by a plane substantially perpendicular to the axis, and a slanted front end defined by a plane oriented relative to the axis at an angle less than 90 degrees;

one V-shaped-end stent comprising a radially expandable mesh structure substantially forming a cylinder having a longitudinal axis, a back end defined by a plane substantially perpendicular to the axis, and a front end defined by the intersection of two planes intersected to form a V-shaped front end as viewed radially;

in which the V-shaped-end stent is implantable in a common branch of a bifurcation of the canal and oriented so that the V-shaped front end extends into the bifurcation; and in which the slanted-end stents are separately implantable in secondary branches of the bifurcation and are oriented so that each slanted front end extends into the bifurcation in abutting relation to the V-shaped front end, thereby providing reinforcing coverage to substantially all affected area of the bifurcation.

2. The system of claim 1 in which the plane defining the slanted front ends is oriented relative to the axis at approximately 50 degrees.

3. The system of claim 1 further comprising radiopaque markers forming a trihedron position on each of said stent.

\* \* \* \* \*